United States Patent
Liao et al.

(10) Patent No.: US 9,241,747 B2
(45) Date of Patent: Jan. 26, 2016

(54) BONE PLATE STRUCTURE, SURGERY DEVICE AND METHOD FOR BONE PLATE IMPLANT

(71) Applicant: Industrial Technology Research Institute, Hsinchu (TW)

(72) Inventors: Chun-Jen Liao, Taipei (TW); Yang-Hwei Tsuang, Taipei (TW); Chia-Hsien Chen, New Taipei (TW); Huang-Chi Chen, Chiayi County (TW)

(73) Assignee: Industrial Technology Research Institute, Hsinchu (TW)

( * ) Notice: Subject to any disclaimer, the term of this patent is extended or adjusted under 35 U.S.C. 154(b) by 154 days.

(21) Appl. No.: 14/109,966

(22) Filed: Dec. 18, 2013

(65) Prior Publication Data
US 2014/0236154 A1   Aug. 21, 2014

Related U.S. Application Data

(60) Provisional application No. 61/739,018, filed on Dec. 19, 2012.

(30) Foreign Application Priority Data

Dec. 13, 2013   (TW) .............................. 102146241 A (51) Int. Cl.
| | |
|---|---|
| *A61B 17/56* | (2006.01) |
| *A61B 17/58* | (2006.01) |
| *A61B 17/80* | (2006.01) |
| *A61B 17/68* | (2006.01) |

(Continued)

(52) U.S. Cl.
CPC ......... *A61B 17/8061* (2013.01); *A61B 17/1728* (2013.01); *A61B 17/808* (2013.01)

(58) Field of Classification Search
None
See application file for complete search history.

(56) References Cited

U.S. PATENT DOCUMENTS

| | | |
|---|---|---|
| 6,096,040 A | 8/2000 | Esser |
| 6,358,250 B1 | 3/2002 | Orbay |

(Continued)

FOREIGN PATENT DOCUMENTS

| | | |
|---|---|---|
| CN | 1523972 | 8/2004 |
| CN | 1589750 | 3/2005 |

(Continued)

OTHER PUBLICATIONS

"Office Action of China Counterpart Application", issued on Jun. 26, 2015, p. 1-p. 13.

(Continued)

*Primary Examiner* — Sameh Boles
(74) *Attorney, Agent, or Firm* — Jianq Chyun IP Office (57) ABSTRACT

A bone plate structure adapted to fix a bone in an affected part is provided. The bone plate structure includes first and second bone plates. The first bone plate has a first stacking portion and a first extending portion and is adapted to be moved onto the bone through a wound of the affected part. The second bone plate has a second stacking portion and a second extending portion and is adapted to be moved onto the bone through the wound. When the first and second bone plates are located on the bone, the second bone plate is adapted to be moved relatively to the first bone plate, such that the first and second stacking portions are stacked with each other and the first and second extending portions are expanded relatively. A surgery device and a method for bone plate implant suitable for the bone plate structure is also provided.

16 Claims, 10 Drawing Sheets

(51) Int. Cl.
*A61F 2/30* (2006.01)
*A61B 17/17* (2006.01)

(56) References Cited

U.S. PATENT DOCUMENTS

| | | |
|---|---|---|
| 6,364,882 B1 | 4/2002 | Orbay |
| 6,866,665 B2 | 3/2005 | Orbay |
| 8,231,662 B2 | 7/2012 | Huebner |
| 2004/0181226 A1 | 9/2004 | Michelson |
| 2006/0089648 A1 | 4/2006 | Masini |
| 2006/0229619 A1 | 10/2006 | Orbay et al. |
| 2009/0088767 A1 | 4/2009 | Leyden et al. |
| 2009/0228047 A1 | 9/2009 | Derouet et al. |
| 2009/0275987 A1* | 11/2009 | Graham ............... A61B 17/80 606/280 |
| 2009/0312803 A1 | 12/2009 | Austin et al. |
| 2012/0010667 A1 | 1/2012 | Eglseder |
| 2012/0016366 A1 | 1/2012 | Eglseder |

FOREIGN PATENT DOCUMENTS

| | | |
|---|---|---|
| CN | 101365393 | 2/2009 |
| CN | 101662994 | 3/2010 |
| DE | 10131992 | 1/2003 |
| EP | 0999796 | 4/2003 |
| EP | 1985249 | 10/2008 |
| TW | M380787 | 5/2010 |
| TW | M411219 | 9/2011 |
| WO | 02067795 | 9/2002 |

OTHER PUBLICATIONS

Alexander Geoffrey McQuinn, et al., "Risk Factors for Redisplacement of Pediatric Distal Forearm and Distal Radius Fractures," J Pediatr Orthop, vol. 32, No. 7, Oct./Nov. 2012, pp. 687-692.

Sang Ki Lee, et al., "Distal Ulna Hook Plate Fixation for Unstable Distal Ulna Fracture Associated With Distal Radius Fracture," Orthopedics, vol. 35, No. 9, Sep. 2012, pp. e1358-e1364.

Louis F. Amorosa, et al., "A functional outcomes survey of elderly patients who sustained distal radius fractures," Springer Hand, Mar. 8, 2011, pp. 260-267.

Derek H. Park, et al., "Volar Plating for Distal Radius Fractures—Do Not Trust the Image Intensifier When Judging Distal Subchondral Screw Length," Techniques in Hand & Upper Extremity Surgery, vol. 16, No. 3, Sep. 2012, pp. 169-172.

Peter C. Rhee, et al., "Minimally Invasive Flexible Insertion and Rigid Intramedullary Nail Fixation for Distal Radius Fractures," Techniques in Hand & Upper Extremity Surgery, vol. 16, No. 3, Sep. 2012, pp. 159-165.

Michael Osti, et al., "Locking Versus Nonlocking Palmar Plate Fixation of Distal Radius Fractures," Orthopedics, vol. 35, No. 11, Nov. 2012, pp. e1613-e1617.

Alvin Chao-Yu Chen, et al., "Design optimisation and experimental evaluation of dorsal double plating fixation for distal radius fracture," Injury, Sep. 24, 2012, pp. 527-534.

Michiel A. J. van de Sande, et al., "Surgical Technique: Tibia Cortical Strut Autograft Interposition Arthrodesis After Distal Radius Resection," Clinical Orthopaedics and Related Research, Sep. 22, 2012, pp. 803-813.

* cited by examiner

BONE PLATE STRUCTURE, SURGERY DEVICE AND METHOD FOR BONE PLATE IMPLANT

CROSS-REFERENCE TO RELATED APPLICATION

This application claims the priority benefits of U.S. provisional application Ser. No. 61/739,018, filed on Dec. 19, 2012 and Taiwan application serial no. 102146241, filed on Dec. 13, 2013. The entirety of each of the above-mentioned patent applications is hereby incorporated by reference herein and made a part of this specification.

TECHNICAL FIELD

The disclosure is related to a bone plate structure, a surgery device and a method for a bone plate implant, more particularly related to a bone plate structure including a plurality of bone plates, and a surgery device and a method for a bone plate implant suitable for the bone plate structure.

BACKGROUND

In the field of orthopaedic medical treatment, there are various kinds of medical treatment for bone injury, wherein fixing the injured bone by using a bone plate in order to heal over the injured bone is most commonly known. Taking a portion of a human arm as an example, the human arm has a plurality of bones with different shapes, such as a radius, a humerus, and the like, and the distal radius of human being is one of the portions easy to cause bone fracture.

At present, in the surgical operation of medical treatment for distal radius fracture, in order to actually fix the injured distal radius by using a bone plate structure, the bone plate structures are generally in a single structure with having a maximum outer diameter at its end, such as T-shaped structures, Y-shaped structures, or the like. Therefore, a large surgical wound operation is required such that the bone plate structure can be implanted and fixed onto the distal radius. However, the large surgical wound operation may seriously destroy the soft tissues around the wrist, and the activity of the wrist may also be adversely affected after surgery.

SUMMARY

The disclosure provides a bone plate structure which is adapted to be implanted into an affected part and fixed onto a bone through a minimally invasive surgery.

The disclosure provides a surgery device which is adapted for implanting a bone plate structure into an affected part and fixing it onto a bone through a minimally invasive surgery.

The disclosure provides a method for implanting a bone plate which is adapted for implanting a bone plate structure into an affected part and fixing it onto a bone through a minimally invasive surgery.

The bone plate structure of the disclosure is adapted to fix a bone in an affected part. The bone plate structure includes a first bone plate and a second bone plate. The first bone plate has a first stacking portion and a first extending portion and is adapted to be moved onto the bone through a wound of the affected part. The second bone plate has a second stacking portion and a second extending portion and is adapted to be moved onto the bone through the wound of the affected part. When the first bone plate and the second bone plate are located on the bone, the second bone plate is adapted to be moved relatively to the first bone plate, such that the first stacking portion and the second stacking portion are stacked with each other. When the first stacking portion and the second stacking portion are stacked with each other, the first extending portion and the second extending portion are expanded relatively.

In one exemplary embodiment of the disclosure, when the first extending portion and the second extending portion are expanded relatively, the maximum outer diameter of the bone structure at the first extending portion and the second extending portion being along a direction is greater than the maximum outer diameter of the first bone plate along the direction and is greater than the maximum outer diameter of the second bone plate along the direction.

In one exemplary embodiment of the disclosure, the maximum outer diameter of the first bone plate along the direction is smaller than 1.5 cm, the maximum outer diameter of the second bone plate along the direction is smaller than 1.5 cm, and when the first extending portion and the second extending portion are expanded relatively, the maximum outer diameter of the bone structure at the first extending portion and the second extending portion being along the direction is greater than 1.5 cm.

In one exemplary embodiment of the disclosure, the first stacking portion has a positioning recess, and when the first stacking portion and the second stacking portion are stacked with each other, the second stacking portion is adapted to be positioned at the positioning recess.

In one exemplary embodiment of the disclosure, the profile of at least one edge of the second stacking portion is closely met with the profile of at least one inner wall of the positioning recess, and when the second stacking portion is positioned at the positioning recess, the edge leans against the at least one inner wall.

In one exemplary embodiment of the disclosure, when the second stacking portion moves to the positioning recess, the inner wall of the positioning recess stops the second stacking portion and the first stacking portion from moving relatively.

In one exemplary embodiment of the disclosure, the bone plate structure has a plurality of openings, and when the first stacking portion and the second stacking portion are stacked with each other, a plurality of fastening elements are adapted to fasten the first bone plate and the second bone plate to the bone through the openings.

In one exemplary embodiment of the disclosure, a portion of the openings are located on the first stacking portion, the other portion of the openings are located on the second stacking portion, and when the first stacking portion and the second stacking portion are stacked with each other, the portion of the openings located on the first stacking portion are aligned to the other portion of the openings located on the second stacking portion respectively.

In one exemplary embodiment of the disclosure, the first bone plate and the second bone plate are adapted to pass through the wound sequentially to move onto the bone.

In one exemplary embodiment of the disclosure, the first bone plate and the second bone plate are pivotally connected to each other, and the first bone plate and the second bone plate are adapted to pass through the wound simultaneously to move onto the bone and to be pivoted relatively on the bone, such that the first stacking portion and the second stacking portion are stacked with each other.

The surgery device of the disclosure is adapted to move the abovementioned bone plate structure into the affected part. The bone plate structure has at least one opening. The surgery device includes a clamping component and at least one guiding component. The clamping component is adapted to clamp the first bone plate and adapted to clamp the second bone plate. The guiding component has at least one through hole and is adapted to be assembled to the clamping component. When the clamping component clamps the first bone plate or the second bone plate and the guiding component is assembled to the clamping component, the through hole extends along an axis and the axis passes through the opening.

In one exemplary embodiment of the disclosure, the through hole is adapted to guide a guiding pipe, such that the guiding pipe extends to the opening.

In one exemplary embodiment of the disclosure, the guiding pipe is adapted to guide a pin, such that the pin passes through the opening and is fixed to the bone.

In one exemplary embodiment of the disclosure, the guiding pipe is adapted to guide a fastening element, such that the fastening element fastens the bone plate structure to the bone through the opening.

In one exemplary embodiment of the disclosure, the opening is located on the first extending portion, and when the clamping component clamps the second bone plate and the first stacking portion and the second stacking portion are stacked with each other, the guiding pipe is adapted to extend to the opening via the guiding of the through hole.

In one exemplary embodiment of the disclosure, the number of the at least one opening is a plurality, the number of the at least one guiding component is two, the two guiding components includes a first guiding component and a second guiding component, when the clamping component clamps the first bone plate and the first guiding component is assembled to the clamping component, the corresponding axis of the through hole of the first guiding component passes through one of the plurality of openings, and when the clamping component clamps the second bone plate and the second guiding component is assembled to the clamping component, the corresponding axis of the through hole of the second guiding component passes through another one of the plurality of openings.

A method for bone plate implant of the disclosure is adapted to fix a bone plate structure onto a bone in an affected part, the bone plate structure has at least one opening, and the method includes the following steps. A surgery device, at least one guiding pipe and a fastening element are provided, wherein the surgery device includes a clamping component and at least one guiding component, the guiding component has a through hole. The guiding component is assembled to the clamping component, the bone plate structure is clamped through the clamping component, and the bone plate structure is moved into the affected part. After the bone plate structure is moved into the affected part, the guiding pipe is guided through the through hole, so that the guiding pipe extends to the opening of the bone plate structure. After the guiding pipe extends to the opening, the fastening element is guided through the guiding pipe, so that the bone plate structure is fastened to the bone by the fastening element via the at least one opening.

In one exemplary embodiment of the disclosure, the method further includes the following steps. A pin is provided. After the guiding pipe extends to the at least one opening, the pin is guided through the guiding pipe, so that the pin passes through the opening and is fixed to the bone.

In one exemplary embodiment of the disclosure, the bone plate structure includes a first bone plate and a second bone plate, the opening is located on the first bone plate, and the step of guiding the guiding pipe through the through hole includes the following steps. When the clamping component clamps the second bone plate and the first bone plate and the second bone plate are stacked with each other partially, the guiding pipe is guided through the through hole, so that the guiding pipe extends to the at least one opening.

In one exemplary embodiment of the disclosure, the bone plate structure includes a first bone plate and a second bone plate, the number of the at least one opening is a plurality, the number of the at least one guiding component is two, the two guiding components include a first guiding component and a second guiding component, the number of the at least one guiding pipe is a plurality, and the step of guiding the guiding pipe through the through hole includes the following steps. When the clamping component clamps the first bone plate and the first guiding component is assembled to the clamping component, one of the plurality of guiding pipes is guided to one of the plurality of openings through the through hole of the first guiding component. When the clamping component clamps the second bone plate and the second guiding component is assembled to the clamping component, another one of the plurality of guiding pipes is guided to another one of the plurality of openings through the through hole of the second guiding component.

In light of the above, the bone plate structure of the disclosure includes a first bone plate and a second bone plate which are adapted to move relatively. During the bone plate structure implant process, the first bone plate having a smaller outer diameter and the second bone plate having a smaller outer diameter may be implanted into the affected part first, then via the relative movement between the first bone plate and the second bone plate which are located in the affected part, the bone structure may be adjusted to be a structure having a larger outer diameter, such that the bone plate structure may be adapted to be fixed with the bone. Accordingly, compared to the conventional bone plate structure which has a larger outer diameter at the end thereof and is a single structure and needs a large surgical wound operation to have the bone plate structure implanted, the bone plate structure of the disclosure may be smoothly implanted into the affected part merely through a minimally invasive surgery. Therefore, the soft tissues around the affected part may be prevented from being seriously destroyed due to the large surgical wound operation, and the activity of the affected part may also be quickly recovered after surgery.

To make the above features and advantages of the disclosure more comprehensible, several embodiments accompanied with drawings are described in detail as follows.

BRIEF DESCRIPTION OF THE DRAWINGS

The accompanying drawings constituting a part of this specification are incorporated herein to provide a further understanding of the disclosure. Here, the drawings illustrate embodiments of the disclosure and, together with the description, serve to explain the principles of the disclosure.

DETAILED DESCRIPTION OF DISCLOSED EMBODIMENTS

Figure 1:
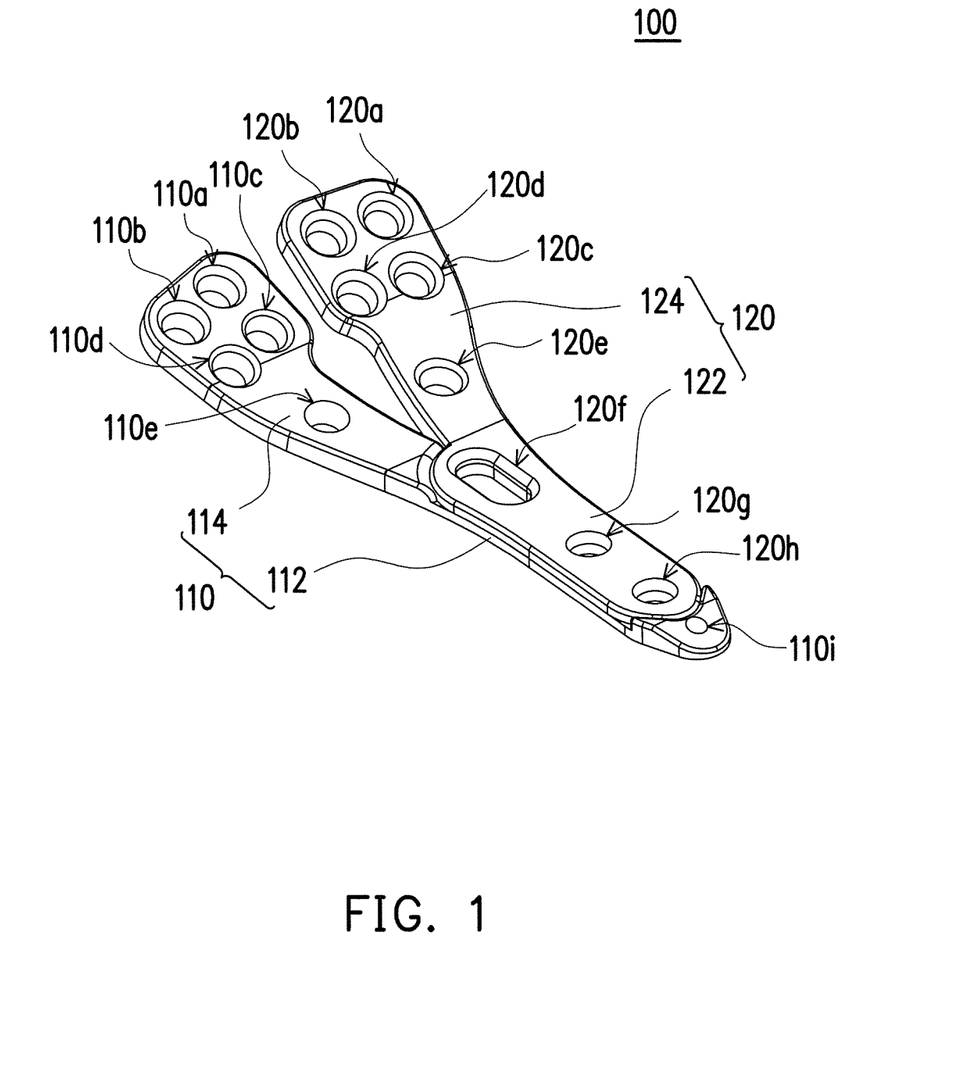
FIG. 1 illustrates a perspective view of a bone plate structure according to one exemplary embodiment of the disclosure.
Figure 2:
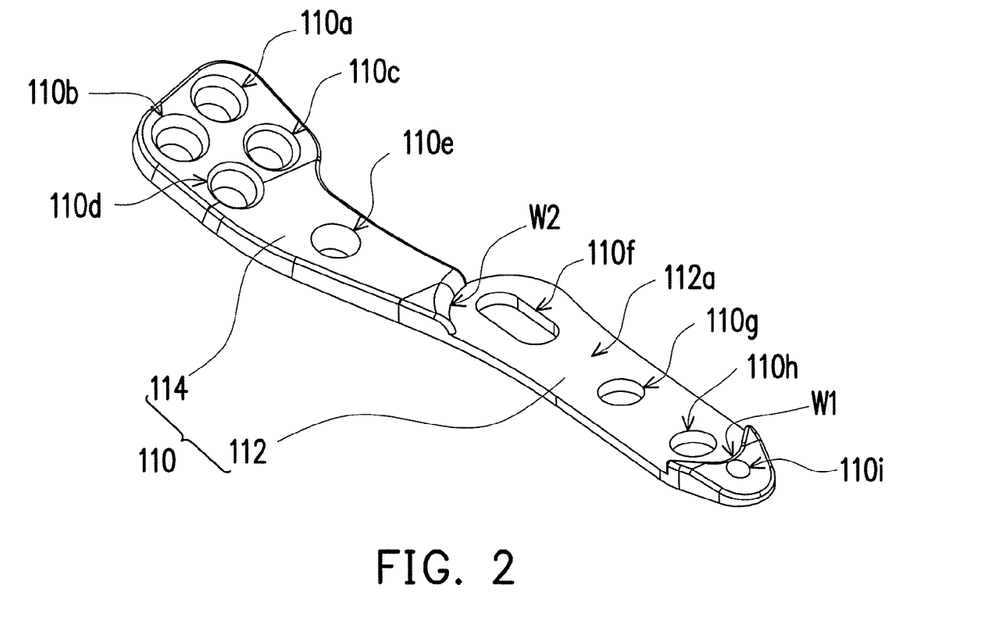
FIG. 2 is a perspective view of a first bone plate in FIG. 1.
Figure 3:
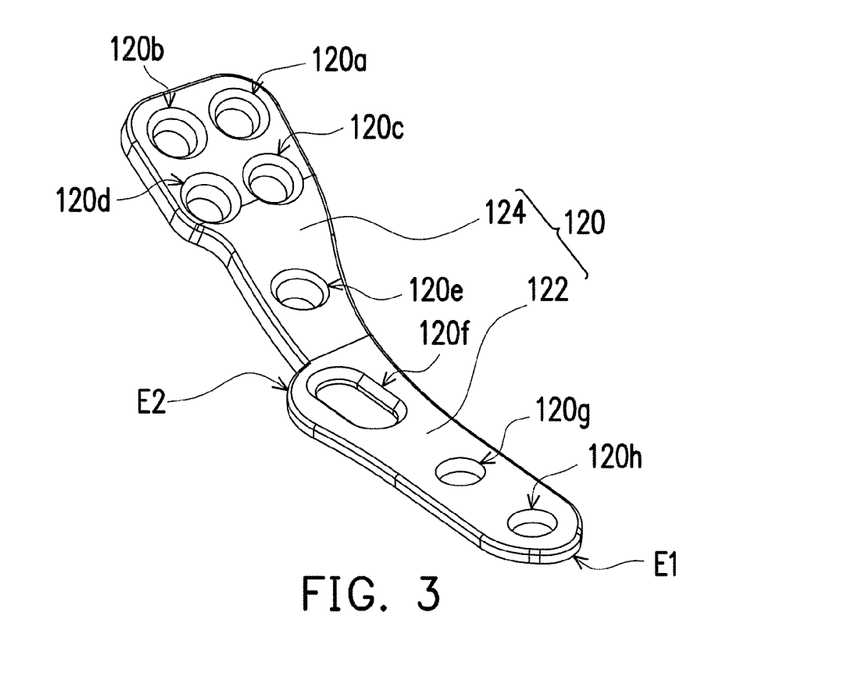
FIG. 3 is a perspective view of a second bone plate in FIG. 1.

FIG. 1 illustrates a perspective view of a bone plate structure according to one exemplary embodiment of the disclosure. FIG. 2 is a perspective view of a first bone plate in FIG. 1. FIG. 3 is a perspective view of a second bone plate in FIG. 1. Referring to FIG. 1 through FIG. 3, the bone plate structure 100 of the embodiment is adapted to fix a bone in an affected part, wherein the bone in the affected part is a distal radius, for example. The bone plate structure 100 includes a first bone plate 110 and a second bone plate 120. The first bone plate 110 has a first stacking portion 112 and a first extending portion 114. The second bone plate 120 has a second stacking portion 122 and a second extending portion 124. The first bone plate 110 and the second bone plate 120 are adapted to form a Y-shaped structure by stacking the first stacking portion 112 and the second stacking portion 122 to each other as shown in FIG. 1, and are adapted to expand relatively as shown in FIG. 2 and FIG. 3. The following describes a method for implanting the bone plate structure 100 into the affected part.

Figure 4A:
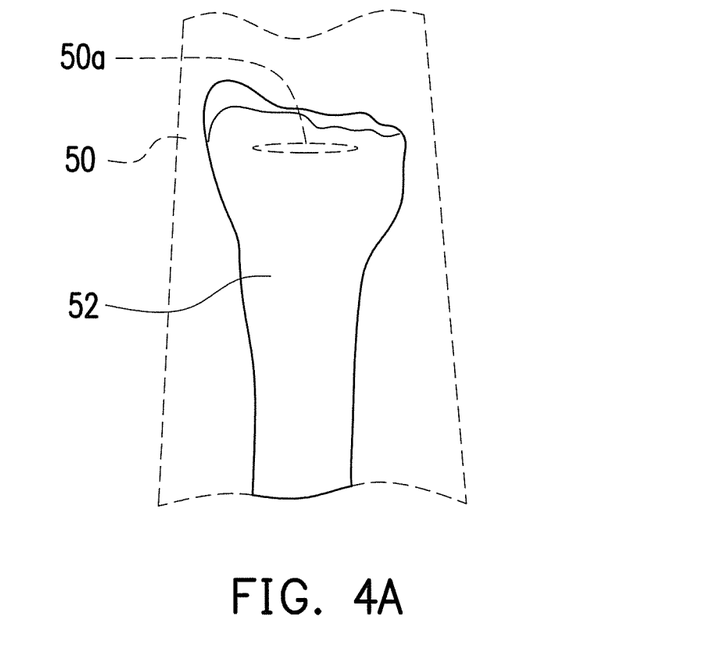
FIG. 4A through FIG. 4E illustrate a flow chart which shows the bone plate of FIG. 1 is implanted into the affected part.
Figure 4B:
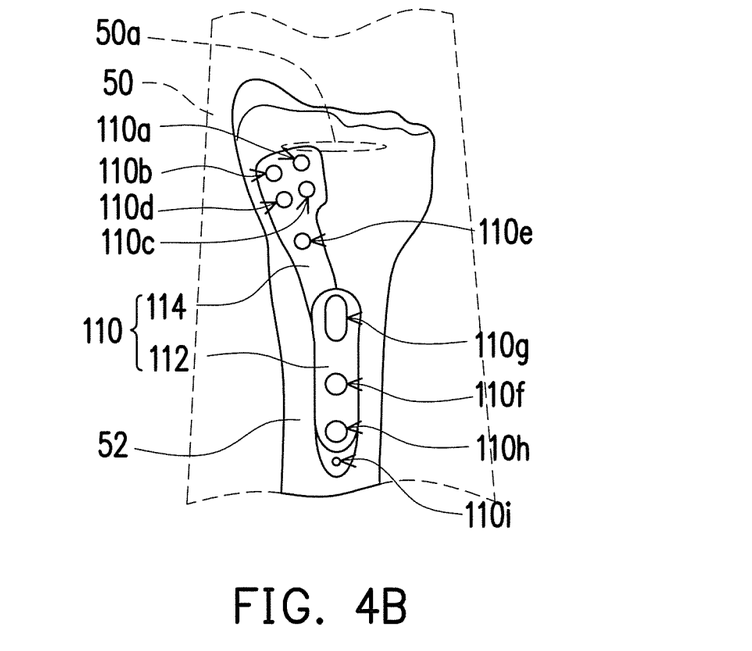
Figure 4C:
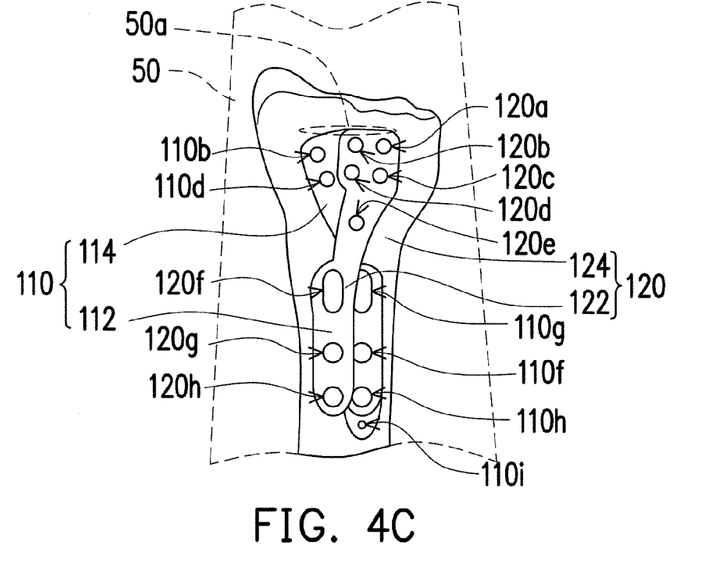
Figure 4D:
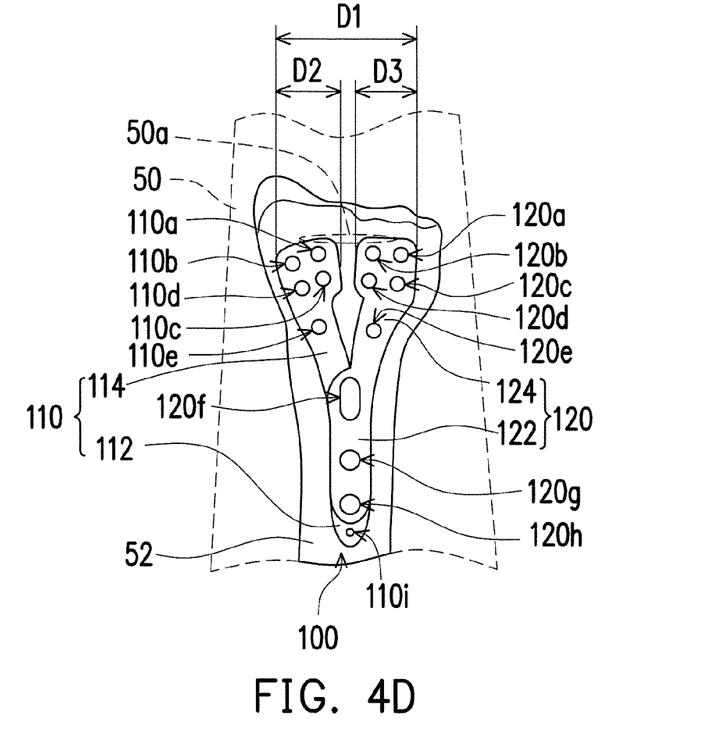

FIG. 4A through FIG. 4E illustrate a flow chart which shows the bone plate of FIG. 1 is implanted into the affected part. For the sake of clearness of the bone and the bone plate structure of the figures, the profiles of the affected part 50 and the wound 50a of FIG. 4A through FIG. 4D are shown in dotted lines. First, as shown in FIG. 4A, the wound 50a is surgically opened at the affected part 50, then as shown in FIG. 4B, the first bone plate 110 is moved onto the bone 52 through the wound 50a of the affected part 50, and the first bone plate 110 is adjusted into a suitable position. Next, as shown in FIG. 4C, the second bone plate 120 is moved onto the bone 52 through the wound 50a, and at this time the second bone plate 120 is not moved to a predetermined position yet. When the first bone plate 110 and the second bone plate 120 are located on the bone 52 as shown in FIG. 4C, a force is applied to the second bone plate 120 so that the second bone plate 120 is adapted to be moved relatively to the first bone plate 110 to reach a position as shown in FIG. 4D, such that the first stacking portion 112 and the second stacking portion 122 are stacked with each other. When the first stacking portion 112 and the second stacking portion 122 are stacked with each other as shown in FIG. 4D, the first extending portion 114 and the second extending portion 124 are expanded relatively. The way of applying a force to the second bone plate 120 so as to move the second bone plate 120 is, for example, applying a force from the outside of the affected part so that the soft tissue of the affected part pushes the second bone plate 120. However, any other suitable way may be used to apply force to the second bone plate 120 in the embodiment, which should not be otherwise construed as a limitation to the disclosure.

Referring to FIG. 4D, when the first extending portion 114 and the second extending portion 124 are expanded relatively, the maximum outer diameter D1 of the bone structure 100 at the first extending portion 114 and the second extending portion 124 being along the extending direction of the wound 50a is greater than the maximum outer diameter D2 of the first bone plate 110 along the extending direction of the wound 50a and is greater than the maximum outer diameter D3 of the second bone plate 120 along the extending direction of the wound 50a. During the process of implanting the bone plate structure 100 into the affected part 50, the first bone plate 110 having a smaller outer diameter and the second bone plate 120 having a smaller outer diameter may be implanted into the affected part 50 first, then via the relative movement between the first bone plate 110 and the second bone plate 120 which are located in the affected part 50, the bone structure 100 may be adjusted to be a structure shown in FIG. 1 and FIG. 4D which has a larger outer diameter, such that the bone plate structure 100 may be adapted to be fixed with the bone 52. Accordingly, compared to the conventional bone plate structure which has a larger outer diameter at the end thereof and is a single structure and needs a large surgical wound operation to have the bone plate structure implanted, the bone plate structure 100 of the disclosure may be smoothly implanted into the affected part 50 merely through a minimally invasive surgery. Therefore, the soft tissues around the affected part 50 may be prevented from being seriously destroyed due to the large surgical wound operation, and the activity of the affected part 50 may also be quickly recovered after surgery.

For instance, when the first extending portion 114 and the second extending portion 124 are relatively expanded as shown in FIG. 4D, the maximum outer diameter D1 of the bone structure 100 at the first extending portion 114 and the second extending portion 124 is greater than 1.5 cm. The outer diameter D2 of the first bone plate 110 is smaller than 1.5 cm, for example. The outer diameter D3 of the second bone plate 120 is smaller than 1.5 cm, for example. Correspondingly, the wound 50a is merely required to be slightly larger than 1.5 cm, so as to complete implanting of the bone plate structure 100.

Referring to FIG. 2, the first stacking portion 112 has a positioning recess 112a in the embodiment. When the first stacking portion 112 and the second stacking portion 122 are stacked with each other as shown in FIG. 1, the second extending portion 122 is adapted to be positioned at the positioning recess 112a of the second extending portion 112. Specifically, the profiles of the edges E1 and E2 of the second stacking portion 122 are closely met with the profiles of the inner walls W1 and W2 of the positioning recess 112a, respectively. When the second stacking portion 122 is moved to and positioned at the positioning recess 112a, the edges E1 and E2 of the second stacking portion 122 lean against the inner walls W1 and W2 of the positioning recess 112a, and the inner walls W1 and W2 of the positioning recess 112a stop the second stacking portion 122 and the first stacking portion 112 from relatively moving.

Figure 4E:
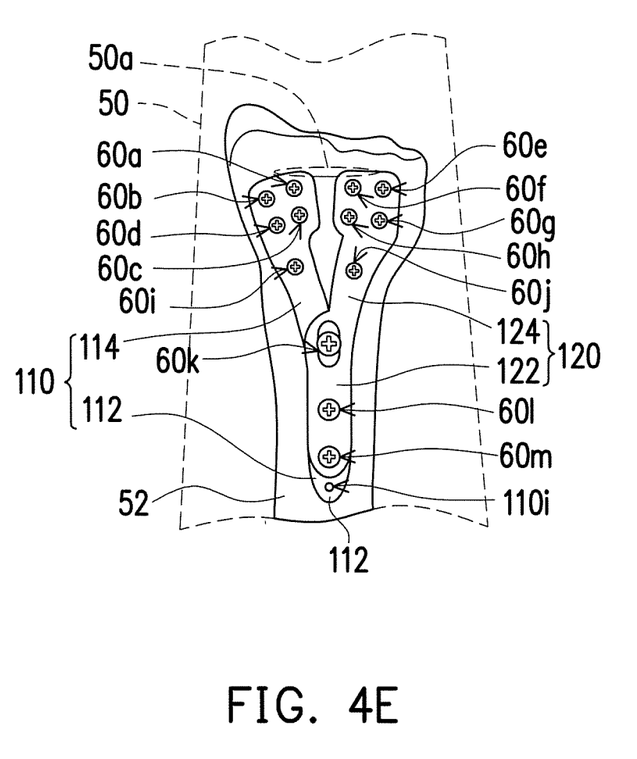

In the embodiment, the bone plate structure 100 has a plurality of openings (indicated as 110a through 110h, and 120a through 120h), wherein the openings 110a through 110e are located on the first extending portion 114, the openings 110f through 110h are located on the first stacking portion 112, the openings 120a through 120e are located on the second extending portion 124, and the openings 120f through 120h are located on the second stacking portion 122. When the first stacking portion 112 and the second stacking portion 122 are stacked with each other as shown in FIG. 1 and FIG. 4D, the openings 110f through 110h located on the first stacking portion 112 are respectively aligned to the openings 120f through 120h located on the second stacking portion 122, and a plurality of fastening elements 60a through 60m fasten the first bone plate 110 and the second bone plate 120 to the bone 52 through the openings 110a through 110h and the openings 120a through 120h as shown in FIG. 4E. The fastening elements 60a through 60m are screws or any other suitable elements for fastening, for example, and the disclosure is not limited thereto.

In the embodiment, through the stacking the second stacking portion 122 of the second bone plate 120 to the first stacking portion 112 of the first bone plate 110, the structural strength of the bone plate structure 100 may be increased. Besides, the shapes of the first bone plate 110 and the second bone plate 120 may be designed according to the exterior shape of the bone 52, such that the bone plate structure 100 may be finely attached to the bone 52, thus the friction between the bone plate structure 100 and the soft tissue of the affected part 50 during the activity of the affected part may further be avoided.

Figure 5:
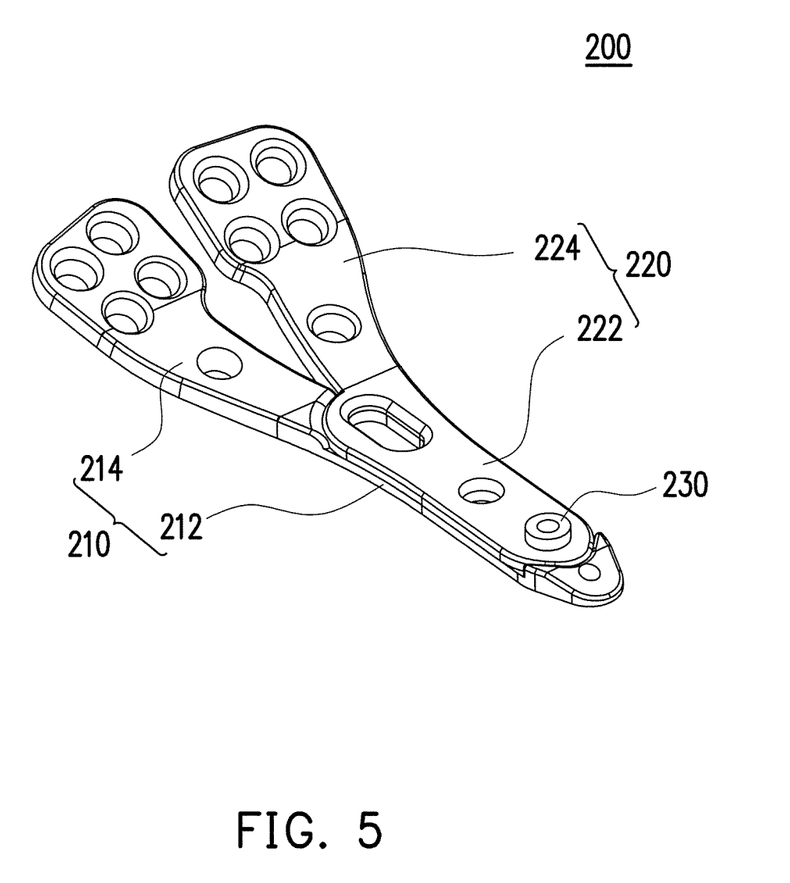
FIG. 5 illustrates a perspective view of a bone plate structure according to another exemplary embodiment of the disclosure.

In the implanting process of the bone plate structure shown in FIG. 4A through FIG. 4E, the first bone plate 110 and the second bone plate 120 of the embodiment may pass through the wound 50a of the affected part 50 sequentially to move onto the bone 52. However, the disclosure is not limited thereto, and it is described with FIG. 5 as an example as follows. FIG. 5 illustrates a perspective view of a bone plate structure according to another exemplary embodiment of the disclosure. In the bone plate structure 200 of FIG. 5, the configuration and function of the first bone plate 210, the first stacking portion 212, the first extending portion 214, the second bone plate 220, the second stacking portion 222, and the second extending portion 224 are similar to that of first bone plate 110, the second bone plate 120, the first stacking portion 112, the first extending portion 114, the second bone plate 120, the second stacking portion 122, and the second extending portion 124 shown in FIG. 1, and it is not repeated herein. The difference between the bone plate structure 200 and the bone plate structure 100 is that the first bone plate 210 and the second bone plate 220 are pivotally connected to each other through a pivoting element 230. The first bone plate 210 and the second bone plate 220 are adapted to be pivoted relatively from the status shown in FIG. 5, then pass through the wound (e.g., the wound 50a of the affected part 50 shown in FIG. 4A) simultaneously to move onto the bone (e.g., the bone 52 shown in FIG. 4A) and to be pivoted relatively on the bone to the status shown in FIG. 5, such that the first stacking portion 212 and the second stacking portion 222 are stacked with each other.

Figure 6:
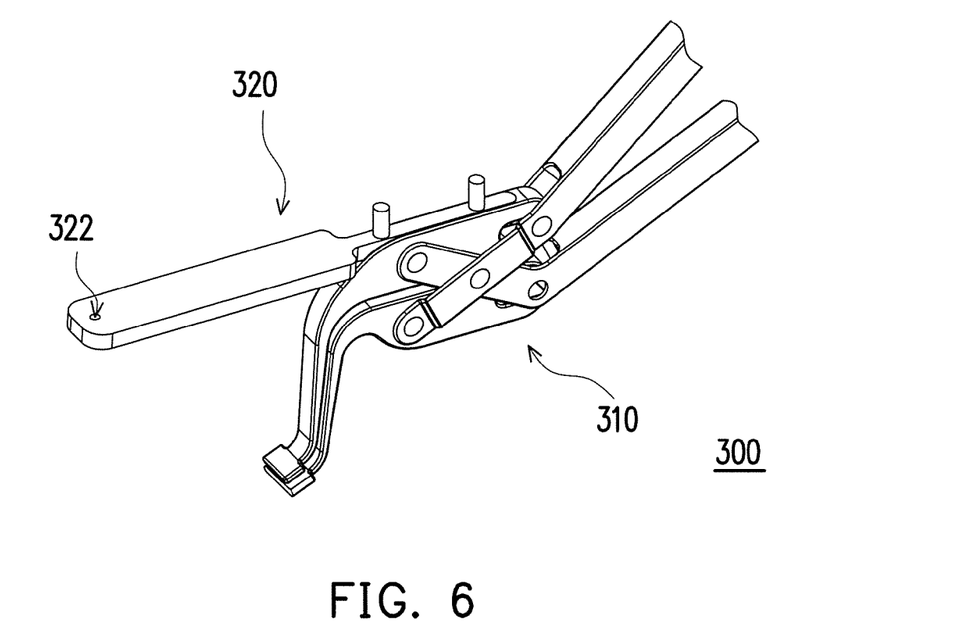
FIG. 6 is a perspective view showing a part of components of a surgery device according to one exemplary embodiment of the disclosure.
Figure 7:
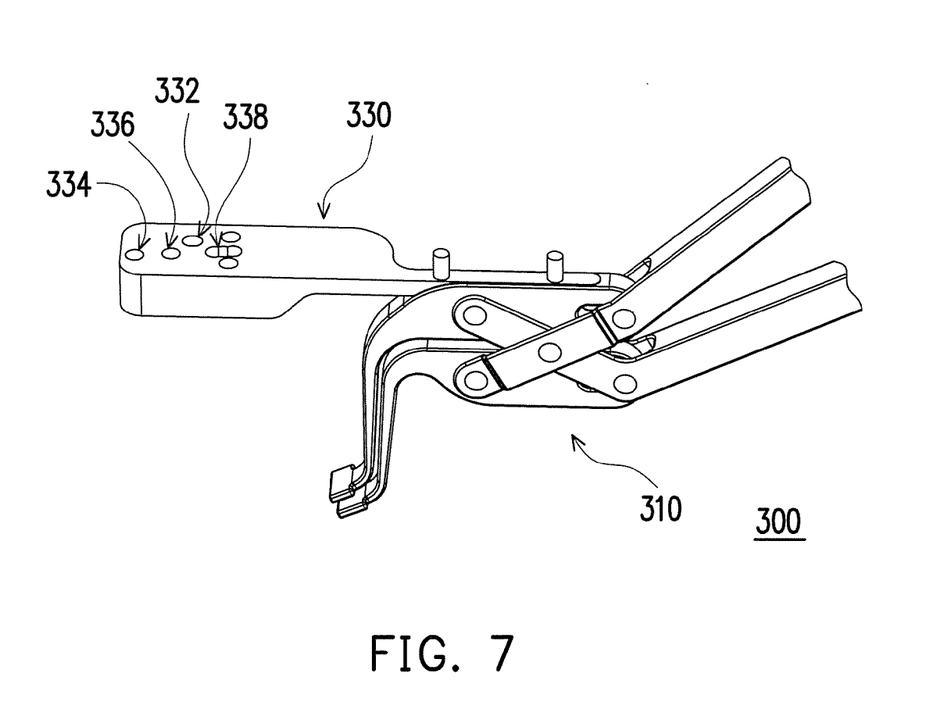
FIG. 7 shows the first guiding component of FIG. 6 is replaced by the second guiding component.

FIG. 6 is a perspective view showing a part of components of a surgery device according to one exemplary embodiment of the disclosure. FIG. 7 shows the first guiding component of FIG. 6 is replaced by the second guiding component. Referring to FIG. 6 and FIG. 7, the surgery device 300 of the embodiment includes a clamping component 310 and two guiding components, the two guiding components are the first guiding component 320 as shown in FIG. 6 and the second guiding component 330 as shown in FIG. 7, respectively. The clamping component 310 is adapted to clamp the first bone plate 110 and the second bone plate 120 shown in FIG. 1 through FIG. 3, and the guiding component 320 and the guiding component 330 are used to assist the aligning and fastening of the first bone plate 110 and the second bone plate 120. The details are as follows.

Figure 8A:
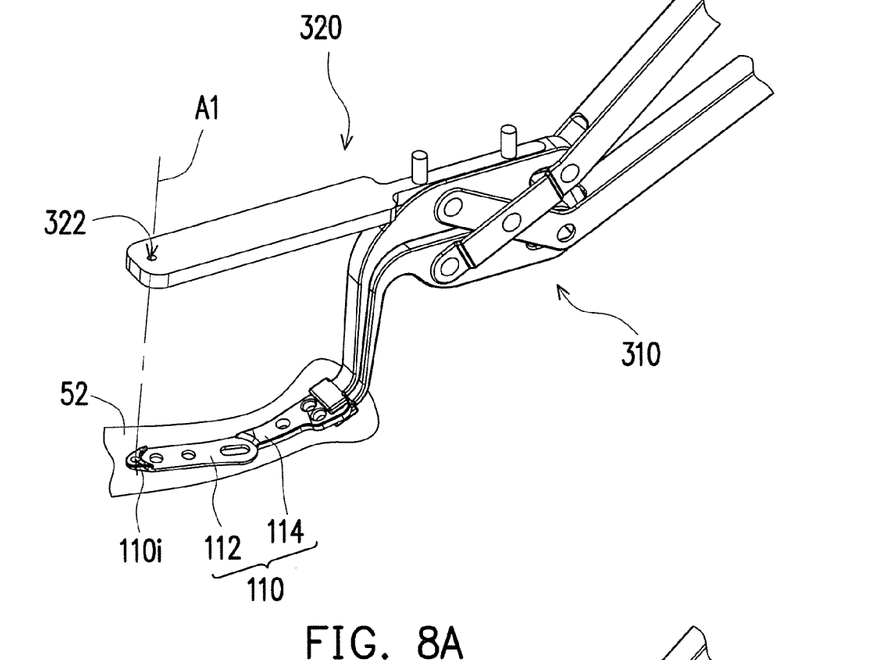
FIG. 8A through FIG. 8F illustrate a flow chart of the operating process of the surgery device of FIG. 6 and FIG. 7.
Figure 8B:
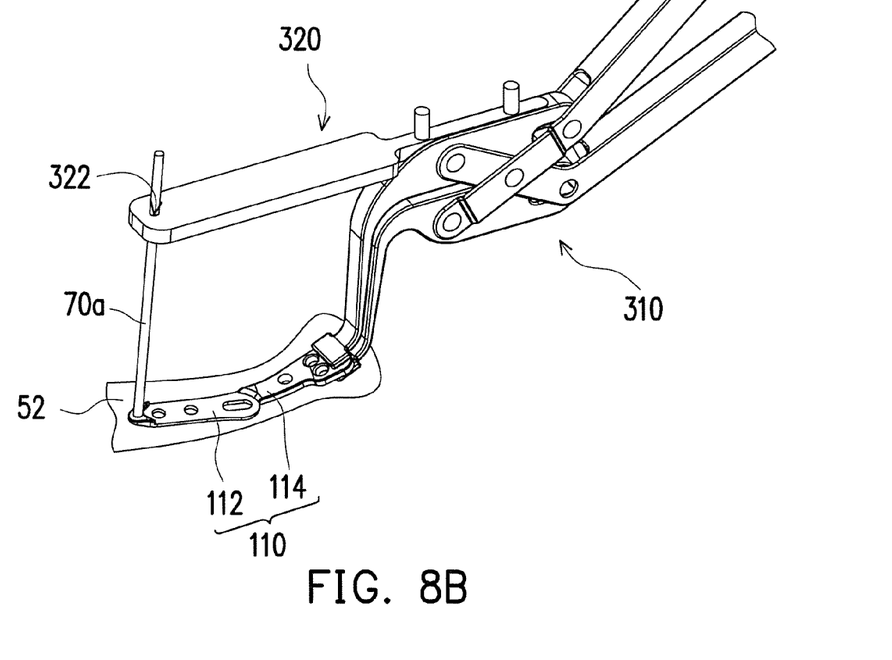
Figure 8C:
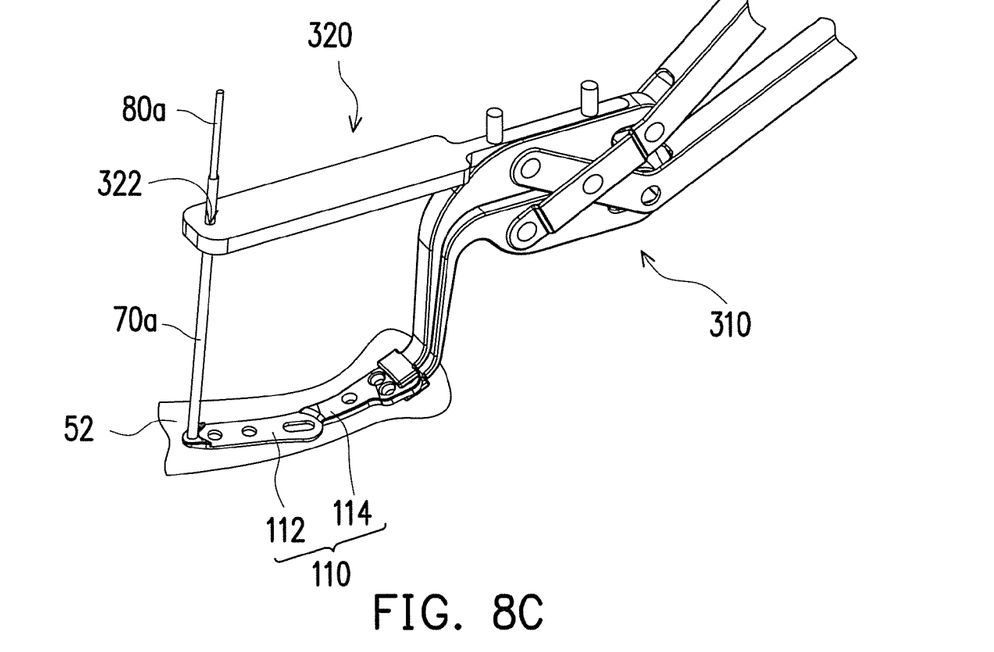

In the embodiment, the first guiding component 320 has at least one through hole 322 (one is shown in the figure) as shown in FIG. 6 and is adapted to be assembled to the clamping component 310. The second guiding component 320 has at least one through hole 332 (plurality are shown in the figure) as shown in FIG. 7 and is adapted to be assembled to the clamping component 310. FIG. 8A through FIG. 8F illustrate a flow chart of the operating process of the surgery device of FIG. 6 and FIG. 7. As shown in FIG. 8A, when the clamping component 310 clamps the first bone plate 110 and the first guiding component 320 is assembled to the clamping component 310, the user may move the first bone plate 110 onto the bone 52 through the wound 50a (shown in FIG. 4A) of the affected part 50 through the clamping component 310, at this time the through hole 322 of the first guiding component 320 extends along an axis A1 and the axis A1 passes through the opening (shown as the opening 110i located on the first bone plate 110) of the bone plate structure 100 (shown in FIG. 1). Accordingly, the through hole 322 may guide a guiding pipe 70a as shown in FIG. 8B, so that the guiding pipe 70a extends to the opening 110i (shown in FIG. 8A), and the guiding pipe 70a may guide a pin 80a as shown in FIG. 8C, so that the pin 80a passes through the opening 110i (shown in FIG. 8A) and is fixed on the bone 52. The pin 80a is a K-pin which is usually used in orthopaedic surgery, for example.

Figure 8D:
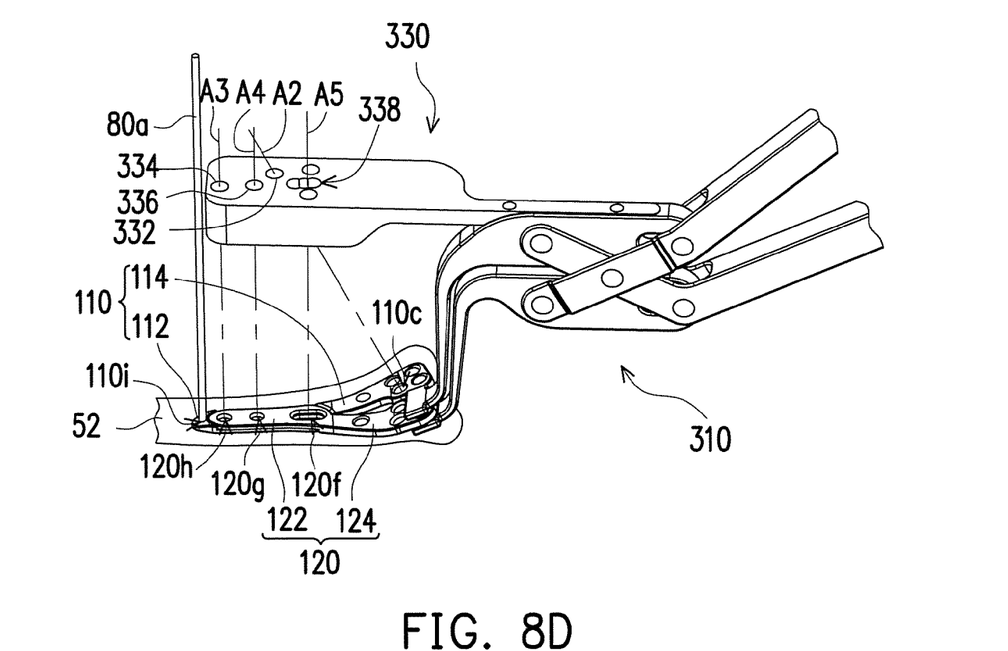
Figure 8E:
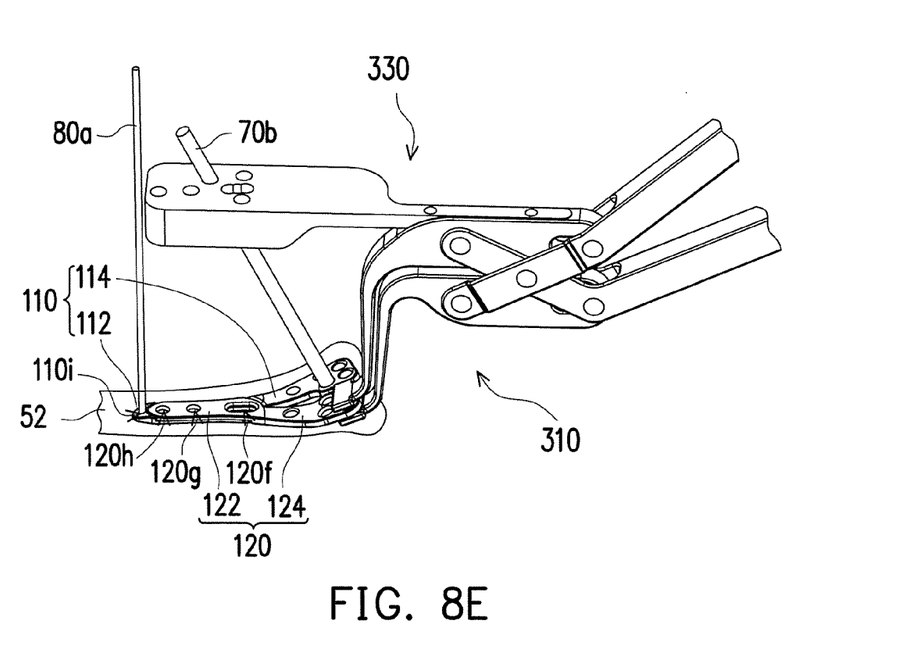

Next, the guiding pipe 70a shown in FIG. 8C is removed, the second guiding component 330 is assembled to the clamping component 310 as shown in FIG. 7, so that the first guiding component 320 is replaced. And the second bone plate 120 is clamped by the clamping component 310 as shown in FIG. 8D and the second bone plate 120 is moved onto the bone 52 through the wound 50a of the affected part 50 (shown in FIG. 4B). After the second bone plate 120 is moved onto the bone 52, the position of the second bone plate 120 is adjusted till the first bone plate 110 and the second bone plate 120 are stacked together (as shown in FIG. 8D). When the clamping component 310 clamps the second bone plate 120 and the first stacking portion 112 and the second stacking portion 122 are stacked with each other, the through hole 332 of the second guiding component 330 extends along an axis A2, and the axis A2 passes through another opening (shown as the opening 110c located on the first stacking portion 114 of the first bone plate) of the bone plate structure 100 (shown in FIG. 1). Accordingly, the through hole 322 may guide a guiding pipe 70b as shown in FIG. 8E, so that the guiding pipe 70b extends to the opening 110c (shown in FIG. 8D), such that the user may ensure that the second bone plate 120 is actually moved onto the predetermined position and stacked on the first bone plate 110.

In addition, when the clamping component 310 clamps the second bone plate 120 as shown in FIG. 8D and the first stacking portion 112 and the second stacking portion 122 are stacked with each other, the through hole 334, the through hole 336 and the through hole 338 of the second guiding component 330 respectively extend along an axis A3, an axis A4 and an axis A5, and the axis A3, the axis A4 and the axis A5 respectively pass through the opening 120h, the opening 120g and the opening 120f of the bone plate structure 120. Accordingly, the through hole 334, the through hole 336, and the through hole 338 may respectively guide a guiding pipe 70c, a guiding pipe 70d and a guiding pipe 70e as shown in FIG. 8F, so that the guiding pipe 70c, the guiding pipe 70d and the guiding pipe 70e respectively extend to the opening 120h, the opening 120g and the opening 120f (shown in FIG. 8D).

Figure 8F:
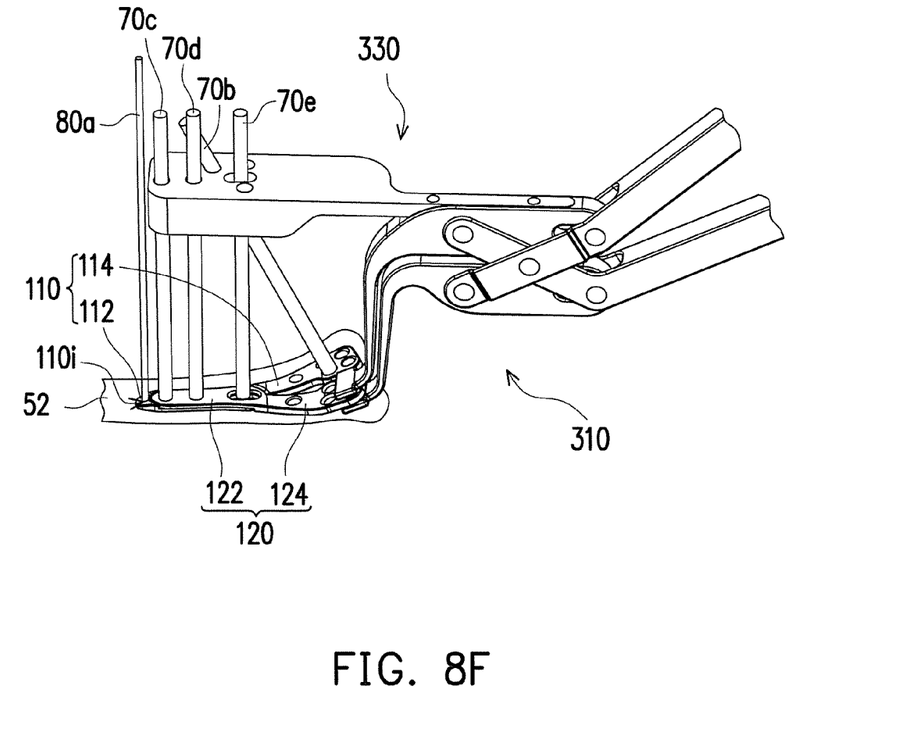

The guiding pipe 70c, the guiding pipe 70d, the guiding pipe 70e and the guiding pipe 70b shown in FIG. 8F may respectively guide the fastening element 60m, the fastening element 60l, the fastening element 60k and the fastening element 60c shown in FIG. 4E, so that the fastening element 60m, the fastening element 60l, the fastening element 60k and the fastening element 60c may fasten the bone plate structure 100 to the bone 52 through the opening 120h, the opening 120g, the opening 120f and the opening 110c, respectively. The other fastening elements shown in FIG. 4E may also be fasten to the bone 52 through the corresponding openings by using similar way, and the disclosure is not limited thereto. Furthermore, more numbers of replaceable guiding components may be used in the fastening of each fastening element, and the disclosure is not limited thereto. After each of the fastening elements is fastened, the surgery device 300 may be removed from the affected part 50 and the pin 80a and all of the guiding pipes are removed, so as to suture the wound 50a.

Through the abovementioned operating method, the fastening elements may accurately fasten the bone plate structure 100 to the bone 52 through the guiding of the corresponding guiding components and the guiding pipes. As such, no image positioning apparatus is required to assist the fastening of the bone plate structure 100, and thus the operating process and the required cost for implanting the bone plate structure 100 may be simplified.

In the embodiment, when the clamping component 310 clamps the first bone plate 110 as shown in FIG. 6, the relative positions between the clamping component 310 and the first bone plate 110 may be fixed by the interference between the clamping component 310 and the openings 110a and 110b (shown in FIG. 1) of the first bone plate 110, for example. Similarly, when the clamping component 310 clamps the second bone plate 120 as shown in FIG. 7, the relative positions between the clamping component 310 and the second bone plate 120 may be fixed by the interference between the clamping component 310 and the openings 120a and 120b (shown in FIG. 1) of the second bone plate 120, for example. As such, the positioning of the first bone plate 110 and the second bone plate 120 may be more accurate. Specifically, the clamping component 310 has positioning protrusions or other suitable structures at the positions corresponding to the openings 110a and 110b or the openings 120a and 120b, so as to position with the openings 110a and 110b or the openings 120a and 120b.

In light of the foregoing, the bone plate structure of the disclosure includes a first bone plate and a second bone plate which are adapted to move relatively. During the bone plate structure implant process, the first bone plate having a smaller outer diameter and the second bone plate having a smaller outer diameter may be implanted into the affected part first, then via the relative movement between the first bone plate and the second bone plate which are located in the affected part, the bone structure may be adjusted to be a structure having a larger outer diameter, such that the bone plate structure may be adapted to be fixed with the bone. Accordingly, compared to the conventional bone plate structure which has a larger outer diameter at the end thereof and is a single structure and needs a large surgical wound operation to have the bone plate structure implanted, the bone plate structure of the disclosure may be smoothly implanted into the affected part merely through a minimally invasive surgery. Therefore, the soft tissues around the affected part may be prevented from being seriously destroyed due to the large surgical wound operation, and the activity of the affected part may also be quickly recovered after surgery. Moreover, the surgery device of the disclosure has a plurality of guiding components which are replaceable and may be assembled to the clamping component, and the fastening elements may accurately fasten the bone plate structure onto the bone through the guiding of the corresponding guiding components and the guiding pipes and through the corresponding openings. As such, no image positioning apparatus or other apparatus is required to assist the fastening of the bone plate structure, and thus the operating process and the required cost for implanting the bone plate structure may be simplified.

Although the disclosure has been described with reference to the above embodiments, it will be apparent to one of ordinary skill in the art that modifications to the described embodiments may be made without departing from the spirit of the disclosure. Accordingly, the scope of the disclosure will be defined by the attached claims and not by the above detailed descriptions.

What is claimed is:

1. A bone plate structure, adapted to fix a bone in an affected part, the bone plate structure comprising: a first bone plate, having a first stacking portion and a first extending portion and adapted to be moved onto the bone through a wound of the affected part; and a second bone plate, having a second stacking portion and a second extending portion and adapted to be moved onto the bone through the wound of the affected part, wherein when the first bone plate and the second bone plate are located on the bone, the second bone plate is adapted to be moved relatively to the first bone plate, wherein the first bone plate and the second bone plate are adapted to form a Y-shaped structure by stacking the first stacking portion and the second stacking portion to each other, wherein when the first stacking portion and the second stacking portion are stacked with each other, the first extending poriton and the second extending portion are expanded relatively.

2. The bone plate structure as claimed in claim 1, wherein when the first extending portion and the second extending portion are expanded relatively, a maximum outer diameter of the bone structure at the first extending portion and the second extending portion being along a direction is greater than a maximum outer diameter of the first bone plate along the direction and is greater than a maximum outer diameter of the second bone plate along the direction.

3. The bone plate structure as claimed in claim 2, wherein the maximum outer diameter of the first bone plate along the direction is smaller than 1.5 cm, the maximum outer diameter of the second bone plate along the direction is smaller than 1.5 cm, and when the first extending portion and the second extending portion are expanded relatively, the maximum outer diameter of the bone structure at the first extending portion and the second extending portion being along the direction is greater than 1.5 cm.

4. The bone plate structure as claimed in claim 1, wherein the first stacking portion has a positioning recess, and when the first stacking portion and the second stacking portion are stacked with each other, the second stacking portion is adapted to be positioned at the positioning recess.

5. The bone plate structure as claimed in claim 4, wherein a profile of at least one edge of the second stacking portion is closely met with a profile of at least one inner wall of the positioning recess, and when the second stacking portion is positioned at the positioning recess, the at least one edge leans against the at least one inner wall.

6. The bone plate structure as claimed in claim 4, wherein when the second stacking portion moves to the positioning recess, an inner wall of the positioning recess stops the second stacking portion and the first stacking portion from moving relatively.

7. The bone plate structure as claimed in claim 1, wherein the bone plate structure has a plurality of openings, and when the first stacking portion and the second stacking portion are stacked with each other and the first extending portion and the second extending portion are expanded relatively, a plurality of fastening elements are adapted to fasten the first bone plate and the second bone plate to the bone through the openings.

8. The bone plate structure as claimed in claim 7, wherein a portion of the openings are located on the first stacking portion, another portion of the openings are located on the second stacking portion, and when the first stacking portion and the second stacking portion are stacked with each other, the openings located on the first stacking portion are aligned to the openings located on the second stacking portion respectively.

9. The bone plate structure as claimed in claim 1, wherein the first bone plate and the second bone plate are adapted to pass through the wound sequentially to move onto the bone.

10. The bone plate structure as claimed in claim 1, wherein the first bone plate and the second bone plate are pivotally connected to each other, and the first bone plate and the second bone plate are adapted to pass through the wound simultaneously to move onto the bone and to be pivoted relatively on the bone, such that the first stacking portion and the second stacking portion are stacked with each other.

11. A surgery device, adapted to move the bone plate structure as claimed in claim 1 into the affected part, the bone plate structure having at least one opening, the surgery device comprising:
 a clamping component, adapted to clamp the first bone plate and adapted to clamp the secod bone plate; and
 at least one guiding component, having at least one through hole and adapted to be assembled to the clamping component, wherein when the clamping component clamps the first bone plate or the second bone plate and the at least one guiding component is assembled to the clamping component, the at least one through hole extends along an axis and the axis passes through the at least one opening.

12. The surgery device as claimed in claim 11, wherein the at least one through hole is adapted to guide a guiding pipe, such that the guiding pipe extends to the at least one opening.

13. The surgery device as claimed in claim 12, wherein the guiding pipe is adapted to guide a pin, such that the pin passes through the at least one opening and is fixed to the bone.

14. The surgery device as claimed in claim 12, wherein the guiding pipe is adapted to guide a fastening element, such that the fastening element fastens the bone plate structure to the bone through the at least one opening.

15. The surgery device as claimed in claim 12, wherein the at least one opening is located on the first extending portion, and when the clamping component clamps the second bone plate and the first stacking portion and the second stacking portion are stacked with each other, the guiding pipe is adapted to extend to the at least one opening via the guiding of the at least one through hole.

16. The surgery device as claimed in claim 11, wherein a number of the at least one opening is a plurality, a number of the at least one guiding component is two, the two guiding components comprises a first guiding component and a second guiding component, when the clamping component clamps the first bone plate and the frist guiding component is assembled to the clamping component, the corresponding axis of the at least one through hole of the first guiding component passes through one of the plurality of openings, and when the clamping component clamps the second bone plate and the second guiding component is assembled to the clamping component, the corresponding axis of the at least one through hole of the second guiding component passes through another one of the plurality of openings.

* * * * *